(12) United States Patent
Bachler et al.

(10) Patent No.: US 8,357,084 B2
(45) Date of Patent: Jan. 22, 2013

(54) STRUCTURE FOR PROBE INSERTION

(75) Inventors: Herbert Bachler, Meilen (CH);
Christian Berg, Uerikon (CH)

(73) Assignee: Phonak AG, Stafa (CH)

( * ) Notice: Subject to any disclaimer, the term of this patent is extended or adjusted under 35 U.S.C. 154(b) by 602 days.

(21) Appl. No.: 12/348,409

(22) Filed: Jan. 5, 2009

(65) Prior Publication Data
US 2009/0112224 A1 Apr. 30, 2009

Related U.S. Application Data

(62) Division of application No. 10/900,879, filed on Jul. 28, 2004, now abandoned.

(51) Int. Cl.
*A61B 5/00* (2006.01)
*A61B 1/00* (2006.01)
(52) U.S. Cl. .................. 600/184; 600/559; 606/108
(58) Field of Classification Search .................. 600/114, 600/184, 200, 202, 203, 208, 128, 559; 606/108
See application file for complete search history.

(56) References Cited

U.S. PATENT DOCUMENTS

| | | | |
|---|---|---|---|
| 4,207,872 A | 6/1980 | Meiri et al. | |
| 4,243,033 A | 1/1981 | DeCaprio et al. | |
| 4,335,713 A * | 6/1982 | Komiya | 600/114 |
| 4,577,621 A | 3/1986 | Patel | |
| 5,345,925 A | 9/1994 | Allred, III et al. | |
| 5,674,196 A | 10/1997 | Donaldson et al. | |
| 5,755,234 A | 5/1998 | Mobley et al. | |
| 5,938,590 A * | 8/1999 | Elliott | 600/184 |
| 5,989,230 A | 11/1999 | Frassica | |
| 6,105,715 A | 8/2000 | Knauer | |
| 6,293,908 B1 | 9/2001 | Fujikura et al. | |
| 6,626,826 B1 | 9/2003 | Van Der Weegen | |
| 2002/0058881 A1 | 5/2002 | Raviv et al. | |
| 2003/0045778 A1 | 3/2003 | Ohline et al. | |
| 2003/0088152 A1 | 5/2003 | Takada | |
| 2003/0171650 A1 | 9/2003 | Tartaglia et al. | |
| 2004/0181128 A1 | 9/2004 | Masters | |
| 2005/0209516 A1 | 9/2005 | Fraden | |

FOREIGN PATENT DOCUMENTS

| | | |
|---|---|---|
| WO | 0216865 A2 | 2/2002 |
| WO | 0216867 A1 | 2/2002 |
| WO | 02091920 A1 | 11/2002 |

* cited by examiner

*Primary Examiner* — Pedro Philogene
(74) *Attorney, Agent, or Firm* — Pearne & Gordon LLP

(57) ABSTRACT

An insert structure is proposed for insertion into an orifice, a canal, a tube and the like of a human or animal creature such as an ear canal, an intestinal tract, a gullet, etc. The insert structure comprises at least one longitudinally extending insert member (3) and a plurality of at least nearly perpendicularly extending further members (5, 7, 9), placed longitudinally at a distance to each other along the insert member, the further members (5, 7, 9) being at least of a flexible and/or soft material.

14 Claims, 3 Drawing Sheets

STRUCTURE FOR PROBE INSERTION

FIELD OF THE INVENTION

The present invention refers to an insert structure for insertion into an orifice, a canal, a tube, etc. of a human or animal body such as an ear canal, an intestinal tract, a gullet, etc. and a method of introducing a sensor, a scanning device, a video head and the like into an orifice, a canal, a tube, etc. of a human or an animal creature.

BACKGROUND OF THE INVENTION

For a proper fit e.g. of a hearing device it has always been considered vital to obtain good data of the ear canal. In case of hearing instruments for hard of hearing patients the data needs to cover a significant part of the canal and preferably beyond the "second bend". Traditionally, data has been obtained with a silicon ear impression and this process is well-established. Being a manual and quite difficult process, alternative technologies have been searched for a long time and currently the focus is on direct scanning of the ear. An intermediate stage is scanning of ear impressions for computer-based in-the-ear (ITE) shell or behind-the-ear (BTE) mold production.

The pursuit of direct ear scanning is still ongoing and there are several approaches being studied. A number of problems remain to be solved, one being the way to insert the scanning head (probe) into the ear canal without hurting the patient, changing the shape of the canal or impacting the data acquisition. This is one of the subjects of the present invention.

In this respect in WO 02/091920 A1 the insertion of a scanning probe into an ear canal is proposed. Therefore, this prior art document is highly relevant and interesting, but does not give any contribution to the above mentioned problem.

In WO 02/16867 A1 a 360° probe-shaped non-contact scanning device is described. It also includes the post-processing of the data to obtain high-precision 3D data for individual ear canal shapes. But again nothing in this prior art document is addressing the issue relating to bends within the ear canal and insertion depth control.

In WO 02/16865 A2 a calibration method for ear scanning probes in order to achieve needed precision is described. The invention itself again does not touch the topic of the present invention.

There are several still open issues and real problems pursuing replacement of traditional ear impression taking by "direct ear scanning" one way or another. Most approaches involve the use of light (LED, laser, etc.); some propose video, ultrasound, computer tomography and even MRI (magnetic resonance imaging). Challenges relate to issues like: resolution, physical reference points, ear canal skin surface condition, post-processing of 3D information and touchless insertion/extraction of probes. The latter problem has not really been solved by any significant patent documents or publications to date and remains an obstacle in obtaining good 3D data of the undistorted ear canal. In addition, there are problems like skin scratches during insertion and extraction and even more severe: harm to the tympanic membrane, which is both very unpleasant and bears the risk of a distorted tympanic membrane function (e.g. conductive hearing loss).

Besides the described problem in relation particularly to insertion into the ear canal, this of course is a general problem in relation to the insertion of any kind of scanning probes, sensors, video heads, tubes like cannulas or catheters etc. into orifices, canals, tubes and the like of the human or animal body. Besides the ear canal this could be e.g. the intestinal tract, the gullet, etc.

SUMMARY OF THE INVENTION

It is therefore a subject of the present invention to propose a solution for introducing in an easy and reliable manner a device such as a scanning device, a sensor, a cannula or catheter, a testing probe, a video head, etc. into an orifice, a canal, a tube, etc. of a human or animal body without causing skin scratching, injuring, harming, etc. of tissues, cartilage or bone skin etc.

According to the present invention an insert structure is proposed. The inventive insert structure for insertion into an orifice, a canal, a tube, etc. of the human or animal body or creature respectively such as an ear canal, an intestinal tract, a gullet of a human or animal being comprises at least one longitudinally extending insert member and a plurality of at least nearly perpendicularly extending further members placed longitudinally at a distance in between the further members along the insert member, the further members being at least of a flexible and/or soft material.

According to a further design the insert member is a tube- or rod-like flexible member.

Again according to a further design it is proposed that the insert member being a tube-like member open at both ends, such that the tube acts like a guidance or supporting structure for the introduction of a sensor, a viewing probe, a scanning probe, a video head, a cannula or catheter, etc. being inserted into the canal or tube of the human or animal being through the tube-like member.

If e.g. optical scanning, viewing or video scanning is planned, it is preferred that the tube-like insert member is transparent, so that viewing, scanning etc. through the tube wall is possible.

Furthermore, according to a further design it is proposed that the at least nearly perpendicularly extending further members are arranged with equal spacing between each other.

Further preferred designs are described in the dependent claims.

Furthermore, a method for introducing a sensor, a scanning probe, a video scanning device, a cannula or catheter, etc. into an orifice, a canal, a tube, etc. of a human or animal body is proposed according to the wording of claim 10. The sensor, the scanning device, etc. can be introduced by using an insert structure as proposed above having a tube-like insert member being open at least on one end. The e.g. pin-like sensor or scanning device can be introduced into the orifice of the tube-like insert member and can be moved within the ear canal or tube of the human or animal body either by moving the insert structure into the canal or tube of the body and/or by moving the sensor within the tube-like insert member.

Again, further preferred methods are described within the dependent claims.

BRIEF DESCRIPTION OF THE DRAWING

The invention will now be explained in more detail based on design examples and with reference to the attached drawings, in which.

DETAILED DESCRIPTION OF THE INVENTION

Figure 1:
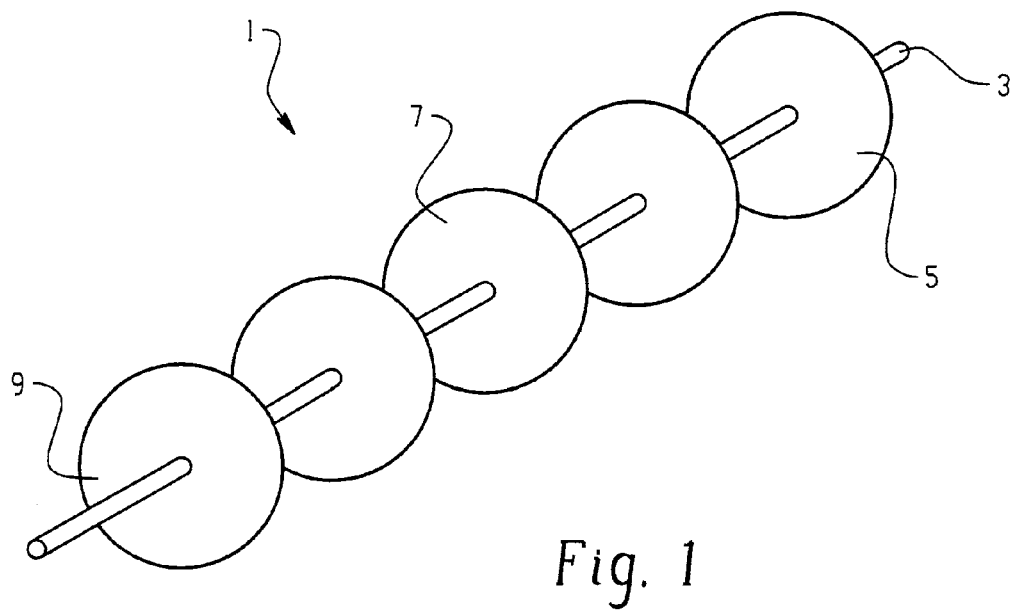
FIG. 1 shows schematically and in perspective view an inventive insert structure.

FIG. 1 shows schematically and in lengthwise perspective view an inventive insert structure 1 mainly comprising a central tube- or rod-like insert member 3, which preferably has to be very flexible. Along the insert member 3 various at least nearly perpendicularly extending further members or disk-like members 5 are arranged, whereby the distance between the various disk-like further members 5 preferably is approx. equal.

It is preferred that at least some of the perpendicularly extending further members or disk-like members are specially marked, like e.g. a first bend marker 7 and a second bend marker 9. Using marked disk-like members it is possible to know at any time the depth of the insertion of the insert member into e.g. an ear canal. Standard markers will give a good indication of the depth of the introduction into the ear canal.

Figure 2:
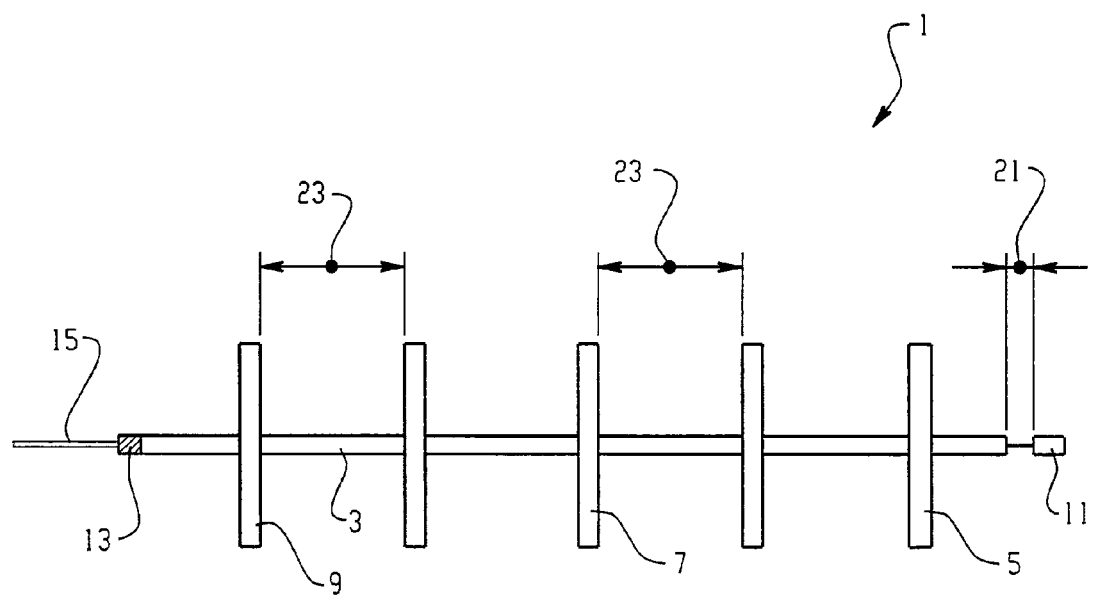
FIG. 2 shows the insert structure of FIG. 1 in a longitudinal section view.

In FIG. 2 the insertion structure 1 of FIG. 1 is shown in a longitudinal section view in more detail. Again, the central insert member 3 is shown, which is preferably a tube with open ends on both sides. Therefore, e.g. an optical sensor probe, such as an optical fiber, is introduced through the tube-like insert member until the tip of the fiber slightly extends beyond the front end of the insert member by a very short distance 21. In case of an ear canal, this distance may be e.g. approx. 2 mm. Such a tip on an optical scanning probe is shown and designated with the reference no. 11 in FIG. 2. In addition again the disk-like members 5, 7 and 9 are shown. The disks are arranged, each at a distance 23 from the next disk-like member, whereby the distance 23 in case e.g. of an ear canal may be approx. 5 mm.

At the back end of the insert member 3 e.g. an electric wire, an optical fiber, etc. 15 can be introduced and be connected through the tube-like insert member 3 with the tip 11 of the optical scanning probe or optical fiber, respectively, extending at the front end of the tube-like insert member.

As already explained in relation to FIG. 1 it is very important always to know the depth of the introduction of the insertion structure into e.g. the ear canal, so that there is no danger of injuring the tympanic membrane or tympanum respectively. Therefore, again in FIG. 2 e.g. the disk-like members 7 and 9 are especially marked.

In order to ensure that an inserted scanning probe 11 does not extend beyond the front end of the insert member 3 by more than a certain predetermined distance 21, a marker 13 can be arranged on the electric wire, optical fiber, etc. 15. This prevents the scanning probe 11 from being inserted too far into e.g. the ear canal, and therefore safeguards the tympanic membrane or tympanum respectively from being injured. The marker 13 can also be a mechanical stopper which is securely attached to the electric wire, optical fiber, etc. 15.

Figure 3:
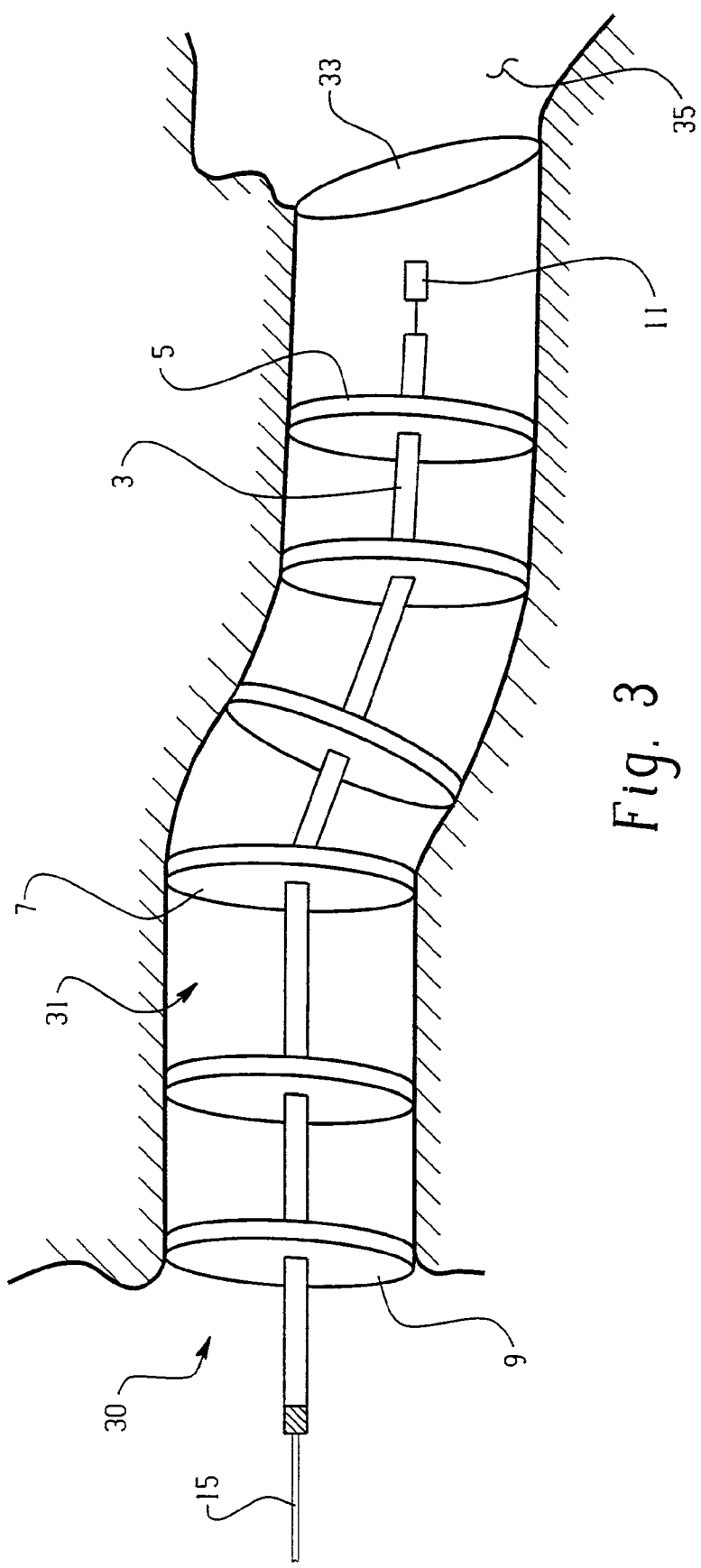
FIG. 3 shows schematically the insertion of an inventive insert structure into an ear canal in a longitudinal section view.

In FIG. 3 it shall now be shown in more detail and based on an example how the insertion structure shall be introduced into e.g. an ear canal.

FIG. 3 shows schematically and in a longitudinal section view an ear canal 31 extending from the ear opening 30 to the tympanic membrane 33 which separates the ear canal 31 from the middle-ear 35.

Looking at FIG. 3 it becomes very obvious that the contours of the ear canal wall are quite complex and furthermore it has to be understood that these contours differ very substantially from one ear canal to another. In other words, an ear canal structure is very individual and the structures may differ quite dramatically from one human or animal being to another.

Therefore, when introducing any kind of a sensor, a scanning device and the like it is very difficult to introduce such a device without injuring or harming the internal skin of the ear canal. Furthermore, it is important that the introduction of such a device is stopped before it reaches the tympanic membrane 33. Both problems, which mean injuring the skin of the ear canal as well as safely inserting the scanning probe through the tube-like insert member 3, are solved by using the inventive insert structure since e.g. the scanning head can never come into contact with the skin of the ear canal. Furthermore, by using marked disk-like members 7 and 9 and/or by using marks on the tube-like insert member one always knows the depth of the insertion of the insert structure. Furthermore, due to the marker 13 arranged on the electric wire, optical fiber, etc. 15 one always knows when the scanning probe which is inserted through the insert tube has reached the front end of the tube-like insert member and one can stop the further insertion of the device.

A further advantage of the inventive structure is that the tube-like member is more or less within the center axis of the ear canal and any kind of scanning of the ear canal structure can be executed in the more or less optimal position of the optical scanning probe, the video camera, the sensor, etc.

But of course, the invention is not at all limited to the introduction of scanning probes or sensors as described above, but it is also possible to introduce cannulas or catheters into at least a first section of the intestinal tract or into the gullet, etc. Also the introduction of cannulas or catheters may cause harm to the skin, e.g. of the intestinal tract, of the gullet and the like.

The flexibility either of the insert member as well as of the disk-like members may be of great importance. Preferably, both members are made out of a flexible material such as e.g. an elastomeric polymer, rubber, silicon rubber, at least partially foamed material, etc. Of course any kind of suitable e.g. polymeric material may be used, the important point is that the material has a high compatibility to skin, is acid resistant and resistant against water. And of course the material should not be toxic even at a very low level.

Furthermore, instead of using the disc-like members, it is also possible to use star-like members or parts comprising perpendicularly extending fingers also made out of an elastomeric polymer, the elastic fingers sliding along the interior wall of the ear canal during the introduction of the insert structure. In that sense it is possible to use any kind spacing members to guide the insert member into the canal or tube, such as e.g. the ear canal.

In summary, the idea of the present invention is to propose a structure that will address and solve the following problems:
  Insertion and extraction of e.g. an ear scanner probe without touching the ear canal independent of the canal shape,
  insertion depth control. There are indicators on the insertion support structure indicating e.g. by color coding insertion depth. E.g. ear canal depth is on average about 28 mm from the first bend with a standard deviation of about 2.6 mm. From the second bend in the canal the average is about 17 mm with a similar standard deviation. Hence there will be no risk to affect the tympanic membrane if the probe extends e.g. 2 mm from the front end of the supporting structure. In addition the probe itself could contain viewing properties such as in case e.g. of a video head, an optical scanner, etc.

Furthermore, an optional solution could be to make the supporting structure transparent to allow recording while pulling the probe out through the tube.

Figure 4:
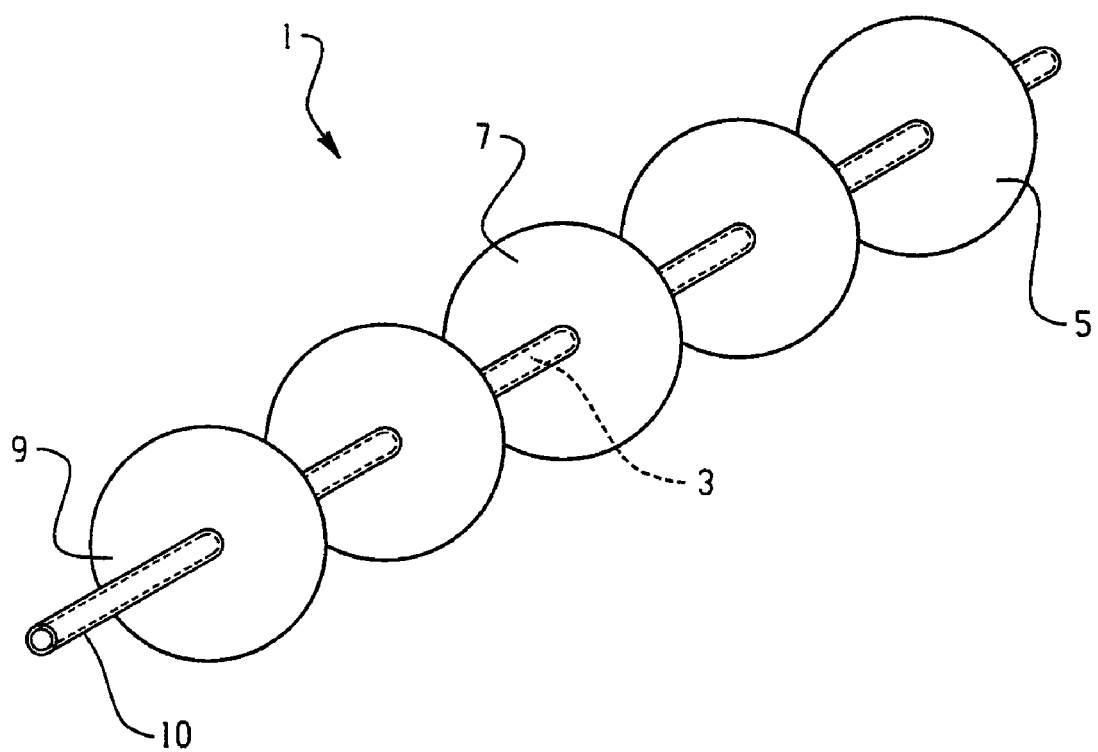
FIG. 4 shows schematically and in perspective view an inventive insert structure, wherein over the outside surface of the insert structure a membrane-like, preferably highly flexible envelope is arranged.

A further solution could be to apply a flexible and possibly disposable membrane or envelope 10 over the whole supporting or insert structure 3, as shown in FIG. 4. This membrane 10 would be slightly pressed towards e.g. the ear canal by the disk-like members such as e.g. the silicon rings on the central insert tube. The probe would then record the membrane shape, which may be provided with a specific pattern and which is prepared to allow optimal e.g. optical scanning. The offset or the difference to the real canal wall data can be corrected by geometric (e.g. thickness of the membrane) and statistical data.

The invention claimed is:

1. A method for scanning contours or structure of an ear canal, comprising:
    introducing a device into a tube of an insert structure, wherein the insert structure comprises at least one longitudinally extending insert member and a plurality of substantially perpendicularly extending further members placed longitudinally at a distance to each other along the insert member and at fixed positions on the insert member, and the further members are made of flexible or soft material;
    inserting the insert structure into the ear canal, wherein the insert member acts as a guidance or supporting structure through which the device is moved while the insert member is inserted and stationary in the ear canal; and
    scanning the contours or the structure of the ear canal by the device.

2. The method according to claim 1, wherein the insert member is a tube-like transparent insert member.

3. The method according to claim 1, wherein the device is movable along the length of the insert member while the insert member is inserted and stationary in the ear canal.

4. The method according to claim 1, wherein the device is movable along the insert member, which is first introduced into the ear canal and wherein said device successively measures the contours or the structure of the ear canal on the entire length of the ear canal to determine 3D data of the ear canal shape.

5. The method according to claim 1, wherein the introduction of the device into the ear canal is stopped before reaching a tympanic membrane.

6. The method according to claim 1, wherein the device is selected from the group consisting of a sensor, a scanning probe and a video scanning device.

7. The method according to claim 1, wherein at least one further member includes a marking to indicate the depth of the insert member into the ear canal.

8. The method according to claim 7, wherein the marking is by color.

9. The method according to claim 1, wherein the device is introduced into the tube of the insert member until a tip of the device extends beyond a front end of the tube.

10. The method according to claim 1, further comprising applying a membrane over the insert structure.

11. The method according to claim 10, wherein the membrane is flexible and disposable.

12. The method according to claim 1, wherein the scanning is optical scanning.

13. The method according to claim 1, wherein the scanning is video scanning.

14. A method for scanning contours or structure of an ear canal, comprising:
    introducing a device into a tube of an insert structure, wherein the insert structure comprises at least one longitudinally extending insert member and a plurality of substantially perpendicularly extending further members placed longitudinally at a distance to each other along the insert member and at fixed positions on the insert member, and the further members are made of flexible or soft material;
    inserting the insert structure into the ear canal, wherein the insert member acts as a guidance or supporting structure through which the device is moved, wherein the device is inserted along the insert member until it reaches a front end of the insert member or a defined position relative to the front end of the insert member, and that the device is moved within the ear canal by moving the device along the insert member; and
    scanning the contours or the structure of the ear canal by the device.

* * * * *